United States Patent [19]
Shealy et al.

[11] Patent Number: 6,023,642
[45] Date of Patent: Feb. 8, 2000

[54] COMPACT TRANSCUTANEOUS ELECTRICAL NERVE STIMULATOR

[75] Inventors: C. Norman Shealy, Fair Grove, Mo.; William A. Tiller, Portola Valley; Jeffrey E. J. Tiller, Boulder Creek, both of Calif.

[73] Assignee: Biogenics II, LLC, Fair Grove, Mo.

[21] Appl. No.: 08/852,932

[22] Filed: May 8, 1997

[51] Int. Cl.[7] .................................................. A61N 1/06
[52] U.S. Cl. ................................................ 607/74; 607/46
[58] Field of Search .............................. 607/46, 47, 58, 607/65, 72, 73, 74

[56] References Cited

U.S. PATENT DOCUMENTS

| | | |
|---|---|---|
| 872,148 | 11/1907 | Raymond et al. . |
| 1,305,725 | 6/1919 | Kent . |
| 3,850,161 | 11/1974 | Liss . |
| 3,902,502 | 9/1975 | Liss et al. . |
| 4,550,733 | 11/1985 | Liss et al. . |
| 4,559,948 | 12/1985 | Liss et al. . |
| 4,574,808 | 3/1986 | Liss et al. . |
| 4,586,509 | 5/1986 | Liss et al. . |
| 4,614,193 | 9/1986 | Liss et al. . |
| 4,627,438 | 12/1986 | Liss et al. . |
| 4,784,142 | 11/1988 | Liss et al. . |
| 4,844,075 | 7/1989 | Liss et al. . |
| 4,856,526 | 8/1989 | Liss et al. . |
| 5,109,847 | 5/1992 | Liss et al. . |
| 5,421,817 | 6/1995 | Liss et al. . |
| 5,609,617 | 3/1997 | Shealy et al. . |

*Primary Examiner*—Scott M. Getzow
*Attorney, Agent, or Firm*—Foley & Lardner

[57] ABSTRACT

An improved compact transcutaneous electrical nerve stimulator (TENS) is provided. The compact TENS of the present invention may be used as a therapeutic device for the reduction of the symptoms of chronic and acute pain. The TENS device includes a power supply and electronics which are packaged to provide a compact, light-weight device which may be worn for an extended period of time by a patient requiring pain relief. Electronic circuitry in the TENS generates an output signal in the form of a positive spike waveform followed by a negative longer duration, lower voltage, waveform. The TENS output signal includes a broad range of frequency components, extending into the gigahertz range. Signal conditioning potentiometers are provided for adjustment of the maximum TENS output signal amplitude. Multiple output channel operation may be provided.

20 Claims, 3 Drawing Sheets

COMPACT TRANSCUTANEOUS ELECTRICAL NERVE STIMULATOR

FIELD OF THE INVENTION

This invention pertains generally to methods and devices used for relieving pain in human subjects, and, more particularly, to transcutaneous electrical nerve stimulators which use electrical stimulation to relieve pain.

BACKGROUND OF THE INVENTION

The sensation of pain is associated with numerous physiological and psychological ailments, and is a universal experience of all complex living organisms. Pain, as the mental manifestation of a neurological response, is an important biological attribute and critical to living and adapting to the environment. Notwithstanding this important role of pain, the alleviation of pain has been a fundamental goal of medicine for as long as the medical profession has existed. Indeed, the ability to control the neurological pathways through which pain is conveyed has made complex procedures far simpler to implement and much less traumatic to the patient.

There is additionally a class of neurological response which is associated with pain that does not correspond to or act as a warning for a particular physical damage or biological dysfunction. In fact, many biologically important transitions are characterized by significant pain, such as the withdrawal period of an addict, during which time the addict's system is depleted of a specific endogenous narcotic. Other mental conditions which are neurological response-dependent conditions include depression, hypertension, causalgia pain, insomnia, and jet lag.

The importance of the ability to control neurological responses and associated perceptions of pain and distress has led to the development of many pain control methodologies. The most common pain control methodologies employ bio-active chemical agents that act to block neurotransmission pathways within the body. These chemicals are designated to operate locally, for spot treatment, or broadly for generalized control or inhibition of the pain response throughout the body. Chemical interference with pain signals has broad based appeal, but in many instances is unacceptable. For example, certain chemicals have toxic side effects or cause allergic reactions in certain patients. For more chronic ailments, such as chronic migraine headache syndrome, continuous absorption of chemical narcotics may reduce the associated pain, but at unacceptably high costs associated with interference with routine activities, addiction, and/or toxicity of the narcotic.

In view of the problems associated with chemical pain control, efforts have focused on treatment approaches which do not involve pharmacological (chemical) interference with neurotransmitters in the body. One such approach involves the use of electrical stimulator devices capable of passing currents across key neurotransmitter junctions in the body, and thus effecting a blockage of neurological pathways which are inducing messages of pain to the brain.

One such electrical stimulator device is the Electreat Transcutaneous Electrical Nerve Stimulator (TENS), manufactured by the Electreat Manufacturing Co., of Minneapolis, Minn. A version of this device was patented in 1919, as U.S. Pat. No. 1,305,725. The Electreat TENS is a therapeutic device which is indicated for the reduction of the symptoms of chronic and acute pain. The device includes a battery power supply, containing two "D" cells connected end-to-end and in series, which delivers 3.0 volts to a coil and interrupter assembly. The interrupter assembly delivers a positive spike waveform which is balanced by a negative long duration low voltage waveform to a transformer, which increases the output voltage level. In the Electreat TENS, the output level may be varied by moving the secondary winding of the transformer in relation to the primary winding of the transformer so as to vary the magnetic coupling between the transformer windings. The output of the Electreat TENS is provided to the tissue of a patient, either directly, using a roller applicator typically associated with the device, or using sponge contact electrodes and cables, which can be connected to the device. It has been found that the electromagnetic structure of the Electreat TENS generates a high voltage spark gap which is a source of a broad range of frequencies, running even into the gigahertz range. The Electreat TENS has been found to be a highly penetrating electrical stimulator for use in relieving acute pain, such as back pain and other post-trauma acute pain episodes of the body. However, the Electreat TENS is a rather large and heavy device, shaped like a long (28 cm) flashlight and weighing over 680 grams.

Another practical implementation of the electrical stimulation approach to pain treatment is disclosed in U.S. Pat. No. 3,902,502, to Liss, et al. The system disclosed in this patent provides a pulsed direct current waveform having a high frequency carrier modulated by a single low frequency modulation. It was discovered that this waveform was particularly successful at controlling symptoms of certain neurological disorders.

U.S. Pat. No. 5,109,847, to Liss, et al., describes an apparatus which generates low current nerve stimulation waveforms to control pain and/or reduce the specific symptoms of certain neurological dysfunctions. This device includes a small DC power source and a means for converting the current output of the power source into a complex waveform as an output across two or more electrodes attached to the patient's body. The complex waveform includes a carrier frequency with at least two low frequency modulations. The carrier frequency ranges between 1 and 100,000 kHz. The first modulation to this carrier has a frequency between 0.01 and 199 kHz. The second modulation to the carrier has a frequency range between 0.1 and 100 kHz. Each modulation to the carrier is pulse trained in the form of a square waveform. This device includes various ancillary systems, such as a low-battery and system-on indicator.

SUMMARY OF THE INVENTION

In accordance with the present invention, an improved compact transcutaneous electrical nerve stimulator (TENS) is provided. The compact TENS of the present invention may be used as a therapeutic device for the reduction of the symptoms of chronic and acute pain. A TENS in accordance with the present invention includes a power supply and electronics which are packaged to provide a compact, lightweight device which may be worn for an extended period of time by a patient requiring pain relief. The electronic circuitry in the compact TENS generates an output signal in the form of a positive spike waveform followed by a negative, longer duration, lower voltage waveform. The TENS output signal includes a broad range of frequency components, extending into the gigahertz range. The TENS output signal may be provided to a patient via electrodes which are placed on the patient in an appropriate location to provide pain relief. The TENS output signal is highly penetrating.

A TENS device in accordance with the present invention includes a compact battery power supply, which may be implemented using two alkaline "C" battery cells connected in series, and placed side-by-side in the device container package. Use of "C" cells in side-by-side position provides for a more compact TENS device.

The compact battery power supply provides power to an electrical circuit which generates the TENS output signal. The primary components of the TENS electrical circuit are a voltage interrupter and a transformer. The voltage interrupter generates an asymmetrical bipolar waveform. The bipolar waveform includes a relatively short duration positive spike waveform signal followed by a longer duration negative signal. The maximum amplitude of the positive spike waveform signal is greater than that of the longer duration negative signal. The asymmetrical bipolar waveform is generated from spark gap generation in the TENS device voltage interrupter. The resulting bipolar waveform contains a wide range of frequency components, extending into the ultra-high frequency, e.g., gigahertz, range. This TENS output signal, including high frequency gigahertz range components, provides highly penetrating electrical stimulation for pain relief.

The bipolar waveform generated by the voltage interrupter is provided to a primary winding of the transformer. The transformer increases the amplitude of the bipolar waveform generated by the voltage interrupter to a higher voltage level, e.g., 115 volts for a 1000 ohm load.

The secondary winding of the transformer is connected via a signal conditioning potentiometer to electrode lead line connector receptacles, e.g., push-pin ports, mounted on a wall of the TENS device package. The signal conditioning potentiometer may be used to adjust the amplitude of the TENS output signal. An adjustment knob may be connected to the potentiometer and mounted on the outside of the TENS device package to allow a user of the TENS device to adjust the potential of the potentiometer and thus the TENS output voltage level.

One or more pairs of electrode lead line receptacles, each pair having its own signal conditioning potentiometer, may be provided in a single compact TENS device package in accordance with the present invention. The availability of multiple adjustable TENS outputs in a single TENS device package provides a multi-channel operating capability. This allows a physician using the device greater flexibility in providing pain relief, and in selecting treatment regimens. For example, two different areas on a patient may be treated for pain relief with a single compact TENS device in accordance with the present invention. The TENS output signals provided to each treatment area may have independently adjusted maximum output voltage levels.

Conventional electrode lead lines and electrodes may be used to connect the TENS device to a patient.

The TENS device of the present invention is packaged to provide a compact, light-weight device which may be worn for an extended period of time by a patient requiring pain relief. For example, a compact TENS device in accordance with the present invention may be packaged into a device container which is no more than approximately 7×11.7×3.6 centimeters in size, and which weighs no more than approximately 454 grams, including the battery power supply. The use of alkaline "C" cell batteries both allows for the reduction of the size and weight of the device, and provides for an extended duration of device operation.

A compact TENS device in accordance with the present invention provides a TENS output signal which provides penetrating electrical stimulation for the relief of the symptoms of chronic and acute pain. Since the device is compact and light-weight, it may be conveniently carried or worn by a patient suffering from such pain. Thus, the compact TENS device of the present invention may be used to provide effective pain relief throughout the day or night without otherwise interfering with the patient's daily activities.

Further objects, features, and advantages of the present invention will be apparent from the following detailed description when taken in conjunction with the accompanying drawings.

DETAILED DESCRIPTION OF THE INVENTION

Figure 1:
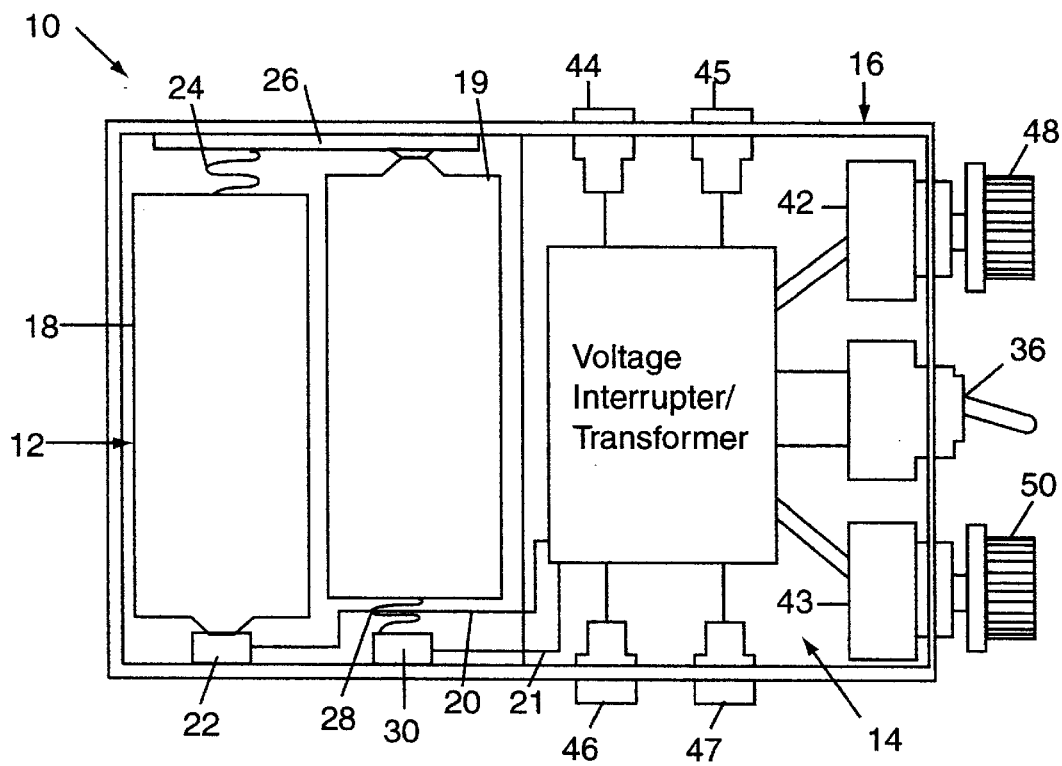
FIG. 1 is a schematic illustration of a compact transcutaneous electrical nerve stimulator (TENS) device in accordance with the present invention, with the side of the TENS device container package opened to show the placement of the power supply and electrical components contained therein.

An exemplary embodiment of an improved compact transcutaneous electrical nerve stimulator (TENS) device in accordance with the present invention is illustrated schematically at 10 in FIG. 1. The TENS device 10 includes a battery power supply 12 and a TENS output signal generating electrical circuit 14, which are contained within a TENS device container package 16. (In FIG. 1, one side of the container package 16 is removed to show the placement of the power supply 12 and electrical circuit 14 therein.) The TENS device package 16 may preferably be formed of hard molded plastic, or similar material. The battery power supply 12 and electrical circuit 14 are designed and placed within the device container package 16 so as to provide a compact TENS device structure. For the exemplary TENS device 10 illustrated in FIG. 1, the overall dimensions of the TENS device are no greater than approximately 7.0×11.7×3.6 centimeters. The battery power supply 12, electrical circuit 14, and packaging 16 components are also selected so as to reduce the overall weight of the TENS device 10. The exemplary TENS device 10 illustrated in FIG. 1, for example, weighs no more than approximately 454 grams, including the battery power supply 12. Thus, in accordance with the present invention, a compact and light-weight TENS device is provided.

The TENS device battery power supply 12 preferably includes two "C" cell batteries 18 and 19. Preferably, alkaline type "C" cell batteries are used. These batteries are small in size, yet provide enough power for extended periods of operation of the TENS device 10. Each battery 18 and 19 provides a nominal 1.5 volt output. The two batteries 18 and 19 are connected in series to provide a nominal 3.0 volt output on lead lines 20 and 21 to the TENS device electrical circuit 14. The batteries 18 and 19 are positioned side-by-side in the device container package 16. This is the most compact battery placement scheme.

The two batteries 18 and 19 may be placed side-by-side and connected electrically in series using the following structure. A positive terminal of battery 18 is placed in contact with a conducting contact pad 22, which, in turn, is connected to the battery power supply lead line 20. The negative terminal of the battery 18 is connected, via an electrically conducting spring 24, to a second electrically conductive contact pad 26. The spring 24 both electrically connects the negative terminal of the battery 18 to the second contact pad 26, and biases the battery 18 against the first contact pad 22, thereby holding the battery 18 in position. The positive terminal of battery 19 is also placed in contact with the electrically conducting contact pad 26. A second electrically conducting spring 28 connects the negative terminal of the second battery 19 to a conducting contact pad 30 which, in turn, is connected to the battery power supply lead line 21. The second electrically conducting spring 28 both electrically connects the negative terminal of the battery 19 to the conducting pad 30, and biases the battery 19 against the conducting pad 26, to hold the battery 19 in place. The use of two alkaline "C" cells placed side-by-side in the TENS device package 16 provides a compact and light-weight power supply 12. It should be noted, however, that other compact light-weight power sources may also be employed, such as a compact 3.6 volt NiCad battery.

Figure 2:
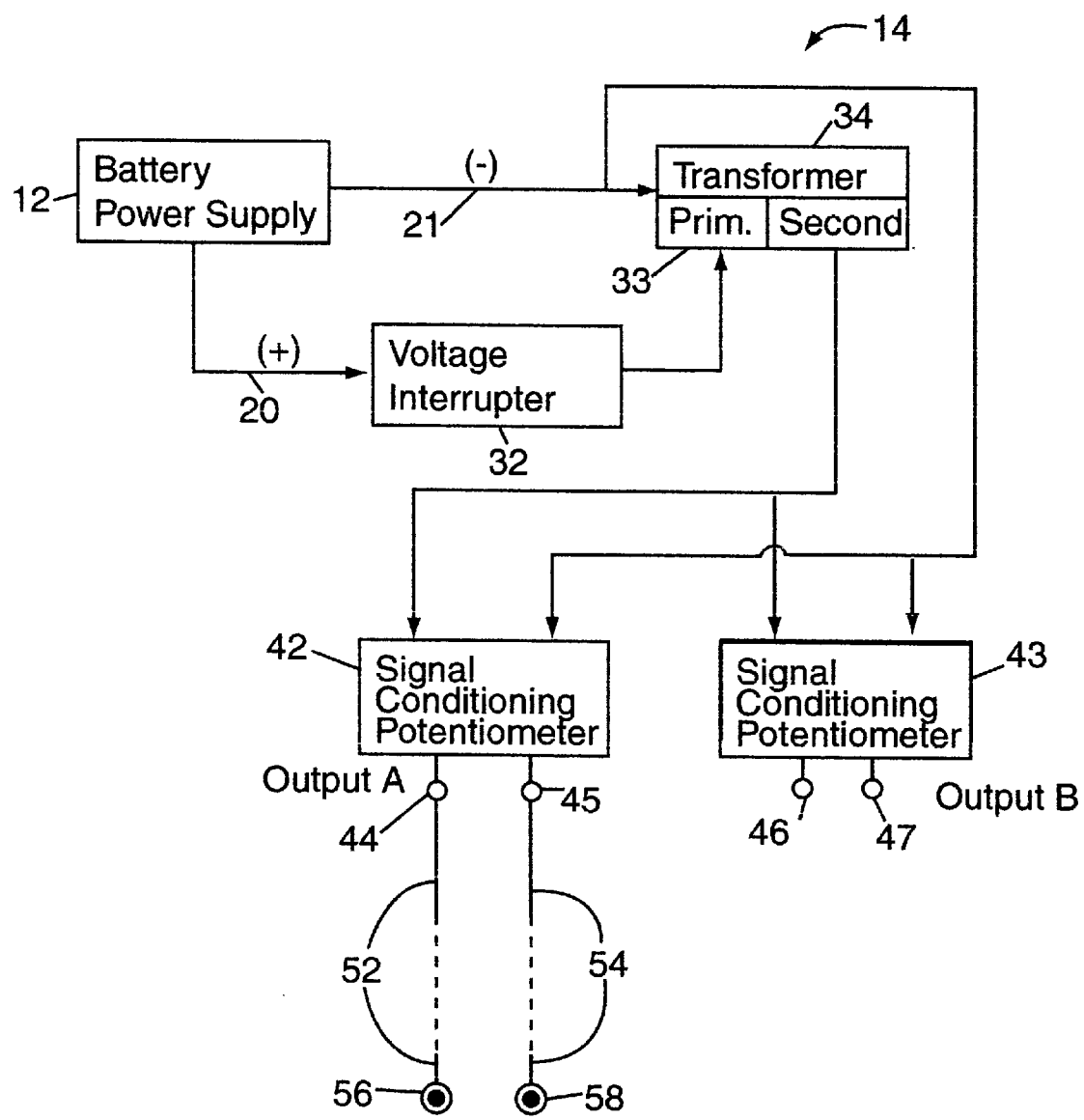
FIG. 2 is a schematic block diagram of an electrical circuit for generating the output signal of a compact TENS device in accordance with the present invention.

The electrical circuit 14 of the TENS device 10 generates the TENS output voltage signal. The TENS device electrical circuit 14 will be described in more detail with reference to the schematic block diagram of FIG. 2 and the schematic circuit diagram of FIG. 3.

The main components of the TENS output signal generating electrical circuit 14 include a voltage interrupter 32 and a transformer 34. The voltage interrupter 32 is connected, via power supply lines 20 and 21, in series with the battery power supply 12 and a primary winding 33 of the transformer 34.

The TENS device 10 may preferably include an on/off switch 36, such as a single pole single throw switch, connected in series between the power supply 12 and the electrical circuit 14. The on/off switch 36 may be closed to turn the TENS device on by applying power from the power supply 12 to the electrical circuit 14. The on/off switch 36 is preferably mounted on a wall of the TENS device container package 16, and extends to an outside thereof. When the on/off switch 36 is closed, an LED 37 may be turned on, to indicate that the TENS device 10 is in operation.

The voltage interrupter 32 generates an asymmetrical bipolar waveform signal from spark gap generation. The voltage interrupter 32 may be implemented as a bounce point contact switch 32 having positive point (adjustable) 38 and negative point (bounce point) 39 electrodes. The electrodes 38 and 39 are normally closed, until sufficient energy builds up in the transformer, operating as a vibrator coil, to pull the bounce point electrode 39 open. As will be discussed in more detail below, an electromagnetic signal is thus generated via gas discharge at the switch electrodes 38 and 39 which contains a broad frequency spectrum, extending into the gigahertz range.

Figure 4:
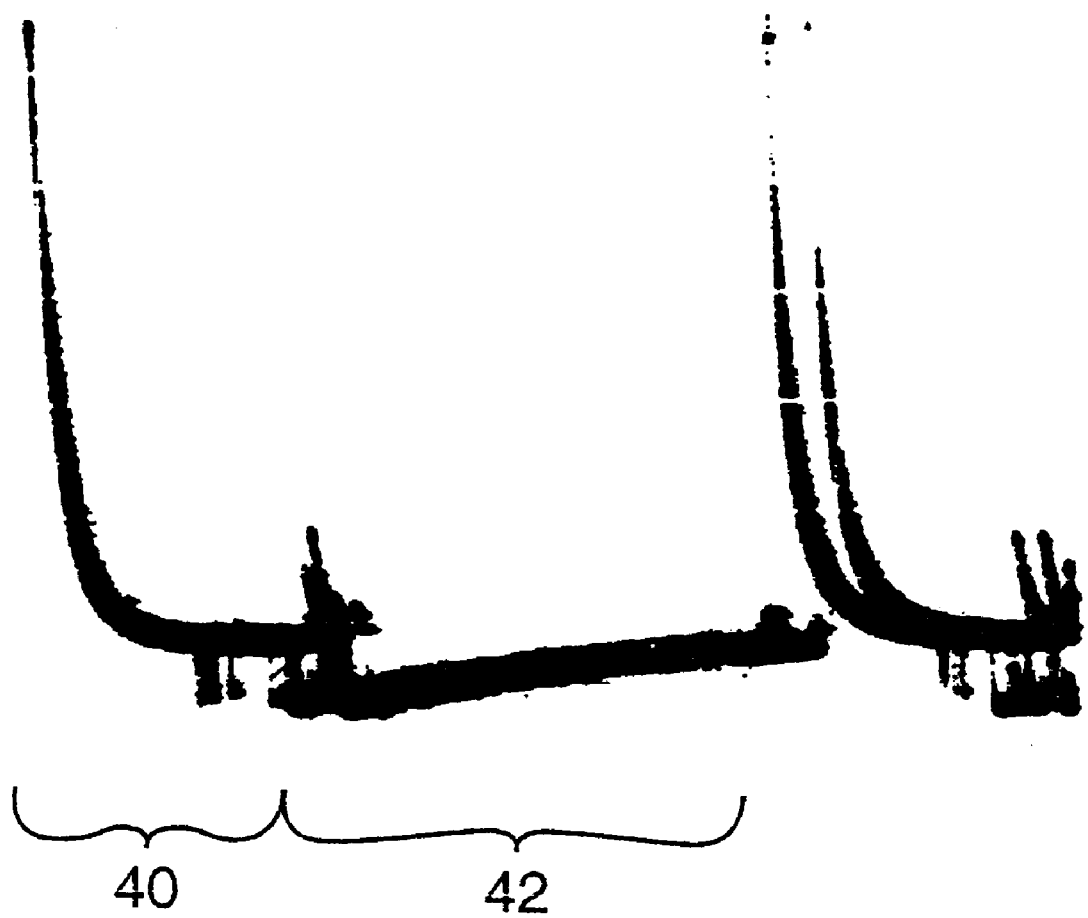
FIG. 4 is an exemplary oscilloscope waveform diagram illustrating the asymmetrical bipolar output waveform of a compact TENS device in accordance with the present invention.

The shape of an exemplary asymmetrical bipolar TENS output signal waveform in accordance with the present invention is illustrated in the oscilloscope trace of FIG. 4. The asymmetrical bipolar waveform signal generated by the voltage interrupter circuit 32 includes a short duration positive spike waveform signal 40, which is balanced by a longer duration negative waveform signal 41. For example, the asymmetrical bipolar waveform pulse may be "on" positively 40 for 2.2 milliseconds and "on" negatively 41 for approximately 4.5 milliseconds. In this case, the resulting asymmetrical bipolar waveform pulse period is approximately 6.7 milliseconds. The corresponding TENS output signal frequency is approximately 150 Hz. A TENS output frequency of 150 Hz+/−30 Hz is preferred. The maximum amplitude of the positive waveform signal 40 is greater than that of the negative waveform signal 41.

As discussed previously, the voltage interrupter 32 generates a high voltage spark gap which is a source of a broad band of frequencies. These frequencies extend even into the gigahertz range. Thus, the asymmetrical bipolar waveform generated by the voltage interrupter includes gigahertz frequency signal components. Preferably, frequency components in the range from 52 to 78 gigahertz are generated in the TENS output voltage waveform. It has been found that the resulting asymmetrical bipolar waveform, including gigahertz range frequency components, provides penetrating electrical stimulation for the relief of chronic and acute pain.

The asymmetrical bipolar waveform generated by the voltage interrupter 32 is a low voltage signal which is provided to the primary winding 33 of the transformer 34. The transformer 34 operates to increase the level of the asymmetrical bipolar waveform generated by the voltage interrupter 32 to a high voltage level at the secondary winding 35 of the transformer 34 which will be provided to a patient to provide pain relief. Of course, the maximum output voltage level across the secondary winding 35 of the transformer 34 will depend on the load to which the TENS output voltage signal is provided. For example, for a 1000 ohm load, the maximum amplitude of the TENS output voltage signal is preferably approximately 115 volts.

Figure 3:
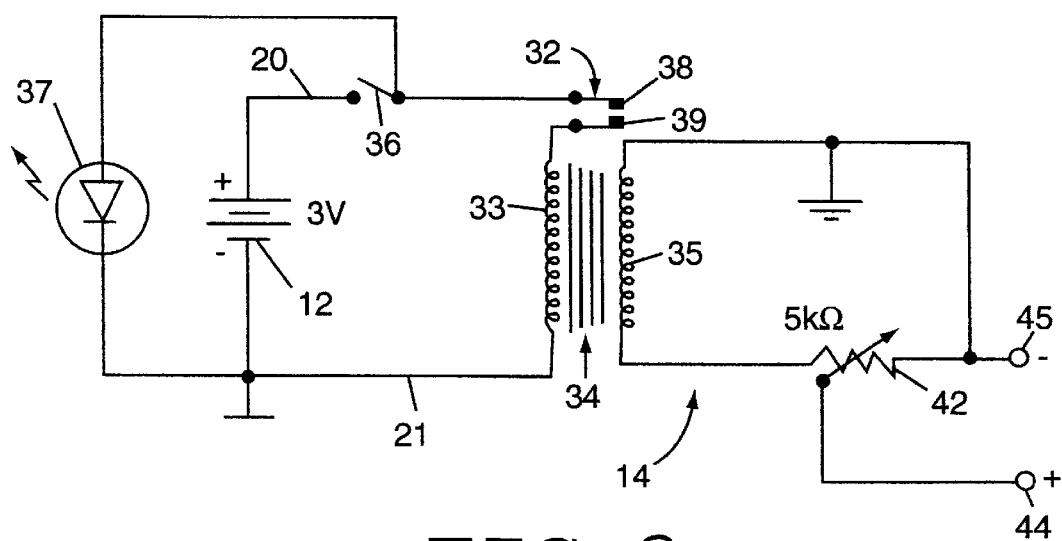
FIG. 3 is a schematic circuit diagram of an electrical circuit for generating the output signal of a compact TENS device in accordance with the present invention.

The high voltage asymmetrical bipolar waveform signal on the secondary winding 35 of the transformer 34 is provided, via signal conditioning potentiometers 42 and 43, to output receptacles 44, 45, 46, and 47. Preferably, two pairs of output receptacles 44 and 45, and 46 and 47, are provided. (Note that only one pair of output receptacles 44 and 45 are shown in FIG. 3.) Each pair of output receptacles 44 and 45, and 46 and 47, is connected to the secondary winding 35 of the transformer 34 by its own signal conditioning potentiometer 42 or 43, respectively. An exemplary potentiometer which may be used to implement the signal conditioning potentiometers 42 and 43 is a 5 thousand ohm linear taper potentiometer. The potential of the signal conditioning potentiometer 42 or 43 is made adjustable to thereby adjust the maximum amplitude of the asymmetrical bipolar TENS output waveform signal provided to the output receptacles 44–47. As the potential of the signal conditioning potentiometer 42 or 43 is increased, the maximum amplitude of the asymmetrical bipolar TENS output waveform signal is reduced.

Returning to FIG. 1, the output receptacles 44–47 are preferably mounted on a wall of the TENS device package 16. Conventional receptacles 44–47, such as push-pin ports, adapted to receive electrode lead line plugs, may be used. Portions of the receptacles 44–47 which are on the outside of the TENS container package 16 are preferably shrouded in an insulating material, such as plastic, to prevent accidental contact with the electrical receptacles themselves.

The signal conditioning potentiometers 42 and 43 are preferably mounted within the TENS device container package 16 to a wall of the container package 16. Potentiometer adjustment knobs 48 and 50 extend outside of the TENS device container package 16, and provide a means for adjustment of the potential of the potentiometers 42 and 43, respectively, by a user of the TENS device 10. As described previously, by adjusting the potential of the potentiometers 42 and 43, the maximum output amplitude of the TENS output waveform signal may be adjusted.

Returning, once again, to FIG. 2. The TENS output signal provided on the output receptacles 44 and 45 is provided to a patient via lead lines 52 and 54, which may include plug ends which are plugged into the receptacles 44 and 45, respectively, and which terminate in electrodes 56 and 58, respectively. Conventional lead lines 52 and 54, and sponge-pad electrodes 56 and 58 may be used. Round, square, or rectangular electrodes 56 and 58 may be used. Exemplary electrodes which may be used include the Flexstim® peel and stick electrodes, made by Perdell International, of San Antonio, Tex., or the ValuTrode-50 self-adhering electrodes, manufactured for Maxxim Medical Henley Home Care of Akron, Ohio. Other types of electrodes and electrode lead lines may also be used in combination with a compact TENS device in accordance with the present invention.

The placement of the electrodes 56 and 58 on a patient will depend on the ailment of the patient, and the treatment regimen. For example, headache therapy may involve the placement of an electrode on the side of the headache at the base of the skull, with the second electrode placed between the thumb and index finger on the web of the hand. Other locations may, of course, also be used.

The preferable availability of two pairs of output receptacles 44 and 45, and 46 and 47, provides for dual-channel operation, and thus more options for treating difficult pain of a patient suffering from multiple pains. Thus, a TENS device 10 in accordance with the present invention, having two pair of output receptacles, provides for the option of one channel operation, wherein a single pair of electrodes are used, the use of three electrodes, wherein a common ground is used on the reference point or the point of pain, or a four electrode, dual-channel, mode of operation, wherein four electrodes are used and the two channels are operated independently to provide pain relieving electrical stimulation.

As has been described, the present invention provides a compact light-weight TENS device. The TENS device of the present invention provides an asymmetrical bipolar TENS output waveform, having an adjustable amplitude, and which includes high frequency components extending into the gigahertz range. The TENS output signal may be provided via electrodes to a patient to provide penetrating electrical stimulation for the relief of acute or chronic pain. Since the TENS device of the present invention is compact and light-weight, it may be conveniently worn or carried by a patient. Thus, a pain treatment regimen may be provided to a patient throughout the day or night, without significantly interfering with the patient's normal activities.

This invention is not confined to the particular examples, embodiments, and applications set forth herein as illustrative, but embraces all such modifications thereof as come within the scope of the following claims.

What is claimed is:

1. A compact transcutaneous electrical nerve stimulator device, comprising:
   (a) a battery power supply including two C cell batteries placed side-by-side and connected together electrically in series;
   (b) a voltage interrupter means for generating an asymmetrical bipolar waveform signal from a spark gap, wherein the voltage interrupter means is connected to the battery power supply, wherein the asymmetrical bipolar waveform signal includes a positive spike waveform signal having a first duration and a first maximum amplitude followed by a negative waveform signal having a second duration which is longer than the first duration and a second maximum amplitude which is less then the first maximum amplitude, and wherein the asymmetrical bipolar waveform signal further includes high frequency signal components in the gigahertz range;
   (c) a transformer having a primary winding and a secondary winding, wherein the primary winding of the transformer is connected to the voltage interrupter means, and wherein the asymmetrical bipolar waveform signal generated by the voltage interrupter means is increased in amplitude by the transformer such that a high voltage asymmetrical bipolar waveform signal is provided on the secondary winding of the transformer;
   (d) a signal conditioning potentiometer connected to the secondary winding of the transformer and including means for adjusting the potential of the signal conditioning potentiometer to adjust the amplitude of the high voltage asymmetrical bipolar waveform signal;
   (e) an electrical receptacle means for connecting the adjusted amplitude high voltage asymmetrical bipolar waveform signal to an electrode lead line and connected to the signal conditioning potentiometer; and
   (f) an enclosing container enclosing the battery power supply, the voltage interrupter means, and the transformer, and wherein the means for adjusting the potential of the signal conditioning potentiometer and the electrical receptacle means extend to an outside of the enclosing container.

2. The device of claim 1 wherein the batteries are alkaline batteries.

3. The device of claim 1 wherein the first duration is approximately 2.2 milliseconds and wherein the second duration is approximately 4.5 milliseconds.

4. The device of claim 1 wherein the asymmetrical bipolar waveform signal includes high frequency signal components in the range of approximately 52 gigahertz to 78 gigahertz.

5. The device of claim 1 wherein the maximum amplitude of the high voltage asymmetrical bipolar waveform signal is approximately 150 volts for a load of 1,000 ohms.

6. The device of claim 1 including a plurality of signal conditioning potentiometers connected to the secondary winding of the transformer, and wherein an electrical receptacle means for connecting the adjusted amplitude high voltage asymmetrical bipolar waveform signal to an electrode lead line is connected to each of the signal conditioning potentiometers to provide for multi-channel operation of the device.

7. The device of claim 1 wherein the means for adjusting the potential of the signal conditioning potentiometer includes an adjustment knob connected to the signal conditioning potentiometer and extending outside of the enclosing container.

8. The device of claim 1 comprising additionally an on/off switch for turning the device on and off.

9. The device of claim 1 wherein the enclosing container is no larger than approximately 7.0 cm×11.7 cm×3.6 cm, and wherein the device weighs no more than approximately 454 grams.

10. The device of claim 1 comprising additionally an electrode lead line connected to the electrical receptacle and an electrode adapted to be connected to a patient connected to the electrode lead line.

11. A compact transcutaneous electrical nerve stimulator device, comprising:

(a) a compact battery power supply;

(b) a voltage interrupter means for generating an asymmetrical bipolar waveform signal from a spark gap, wherein the voltage interrupter means is connected to the battery power supply, wherein the asymmetrical bipolar waveform signal includes a positive spike waveform signal having a first duration and a first maximum amplitude followed by a negative waveform signal having a second duration which is longer than the first duration and a second maximum amplitude which is less then the first maximum amplitude, and wherein the asymmetrical bipolar waveform signal further includes high frequency signal components in the gigahertz range;

(c) a transformer having a primary winding and a secondary winding, wherein the primary winding of the transformer is connected to the voltage interrupter means, and wherein the asymmetrical bipolar waveform signal generated by the voltage interrupter means is increased in amplitude by the transformer such that a high voltage asymmetrical bipolar waveform signal is provided on the secondary winding of the transformer;

(d) a plurality of signal conditioning potentiometers connected to the secondary winding of the transformer, wherein each signal conditioning potentiometer includes means for adjusting the potential of the signal conditioning potentiometer to adjust the amplitude of the high voltage asymmetrical bipolar waveform signal;

(e) an electrical receptacle means for connecting the adjusted amplitude high voltage asymmetrical bipolar waveform signal to an electrode lead line connected to each of the plurality of signal conditioning potentiometers; and (f) an enclosing container enclosing the battery power supply, the voltage interrupter means, and the transformer, and wherein the means for adjusting the potential of the signal conditioning potentiometers and the electrical receptacle means extend to an outside of the enclosing container.

12. The device of claim 11 wherein compact battery power supply includes two C cell alkaline batteries placed side-by-side and connected together electrically in series.

13. The device of claim 11 wherein the first duration is approximately 2.2 milliseconds and wherein the second duration is approximately 4.5 milliseconds.

14. The device of claim 11 wherein the asymmetrical bipolar waveform signal includes high frequency signal components in the range of approximately 52 gigahertz to 78 gigahertz.

15. The device of claim 11 wherein the maximum amplitude of the high voltage asymmetrical bipolar waveform signal is approximately 150 volts for a load of 1,000 ohms.

16. The device of claim 11 wherein the means for adjusting the potential of the signal conditioning potentiometers includes an adjustment knob connected to each of the signal conditioning potentiometers and extending outside of the enclosing container.

17. The device of claim 11 comprising additionally an on/off switch for turning the device on and off.

18. The device of claim 11 wherein the enclosing container is no larger than approximately 7.0 cm×11.7 cm×3.6 cm, and wherein the device weighs no more than approximately 454 grams.

19. A compact transcutaneous electrical nerve stimulator device, comprising:

(a) a battery power supply including two C cell alkaline batteries placed side-by-side and connected together electrically in series;

(b) a voltage interrupter means for generating an asymmetrical bipolar waveform signal from a spark gap, wherein the voltage interrupter means is connected to the battery power supply, wherein the asymmetrical bipolar waveform signal includes a positive spike waveform signal having a first duration and a first maximum amplitude followed by a negative waveform signal having a second duration which is longer than the first duration and a second maximum amplitude which is less then the first maximum amplitude, and wherein the asymmetrical bipolar waveform signal further includes high frequency signal components in the gigahertz range;

(c) a transformer having a primary winding and a secondary winding, wherein the primary winding of the transformer is connected to the voltage interrupter means, and wherein the asymmetrical bipolar waveform signal generated by the voltage interrupter means is increased in amplitude by the transformer such that a high voltage asymmetrical bipolar waveform signal is provided on the secondary winding of the transformer;

(d) a plurality of signal conditioning potentiometers connected to the secondary winding of the transformer, wherein each signal conditioning potentiometer includes an adjustment knob connected to the signal conditioning potentiometer for adjusting the potential of the signal conditioning potentiometer to adjust the amplitude of the high voltage asymmetrical bipolar waveform signal;

(e) an electrical receptacle means adapted for connecting the adjusted amplitude high voltage asymmetrical bipolar waveform signal to an electrode lead line connected to each of the signal conditioning potentiometers;

(f) an on/off switch for turning the device on and off; and (g) an enclosing container enclosing the battery power supply, the voltage interrupter means, and the transformer, wherein the enclosing container is no larger than approximately 7.0 cm×11.7 cm×3.6 cm, and wherein the adjustment knobs for adjusting the potential of the signal conditioning potentiometers, the electrical receptacle means, and the on/off switch extend to an outside of the enclosing container.

20. The device of claim 19 wherein the device weighs no more than approximately 454 grams.

* * * * *